(12) United States Patent
Gao et al.

(10) Patent No.: US 7,281,492 B2
(45) Date of Patent: Oct. 16, 2007

(54) SYSTEM AND METHOD FOR GENERATING A DISCHARGE IN GASES

(75) Inventors: Ju Gao, Champaign, IL (US); Joseph T. Verdeyen, Savoy, IL (US)

(73) Assignee: Advanced Lighting Technologies, Inc., Solon, OH (US)

(*) Notice: Subject to any disclaimer, the term of this patent is extended or adjusted under 35 U.S.C. 154(b) by 0 days.

(21) Appl. No.: 11/082,914

(22) Filed: Mar. 18, 2005

(65) Prior Publication Data

US 2005/0218814 A1    Oct. 6, 2005

Related U.S. Application Data

(63) Continuation-in-part of application No. 10/939,338, filed on Sep. 14, 2004, now Pat. No. 7,126,283, which is a continuation of application No. 10/112,349, filed on Apr. 1, 2002, now Pat. No. 6,791,280.

(60) Provisional application No. 60/553,971, filed on Mar. 18, 2004, provisional application No. 60/648,417, filed on Feb. 1, 2005.

(51) Int. Cl.
*C23C 16/00* (2006.01)
*H05B 41/14* (2006.01)

(52) U.S. Cl. .................. 118/723 E; 315/243

(58) Field of Classification Search .......... 315/111.21, 315/111.81, 241 R, 242, 243, 244–245, 246, 315/248; 118/723 E, 723 ER
See application file for complete search history.

(56) References Cited

U.S. PATENT DOCUMENTS 1,517,466 A * 12/1924 Otto Schaller et al. ..... 315/349

| | | | |
|---|---|---|---|
| 3,942,058 A | 3/1976 | Haugsjaa et al. | |
| 3,942,068 A | 3/1976 | Haugsjaa et al. | |
| 3,943,404 A | 3/1976 | McNeill et al. | |
| 4,240,010 A * | 12/1980 | Buhrer | 315/248 |
| 4,482,246 A | 11/1984 | Meyer et al. | |
| 4,918,031 A | 4/1990 | Flamm et al. | |
| 5,036,252 A * | 7/1991 | Lob | 315/111.31 |
| 5,039,903 A | 8/1991 | Farrall | |
| 5,175,476 A | 12/1992 | Anderson et al. | |
| 5,241,245 A | 8/1993 | Barnes et al. | |
| 5,304,282 A | 4/1994 | Flamm | |
| 5,306,987 A | 4/1994 | Dakin et al. | |
| 5,389,883 A | 2/1995 | Harper | |
| 5,438,235 A | 8/1995 | Sommerer et al. | |
| 5,519,285 A | 5/1996 | Ukegawa et al. | |
| 5,570,179 A | 10/1996 | Weckstrom | |

(Continued)

OTHER PUBLICATIONS

Copies of PCT ISR and WOISA for PCT/US05/09063.

(Continued)

*Primary Examiner*—Shih-Chao Chen
*Assistant Examiner*—Minh Dieu A
(74) *Attorney, Agent, or Firm*—Duane Morris, LLP

(57) ABSTRACT

A method of generating an electrical discharge in a gas contained in a sealed enclosure. The method includes driving a helical coil resonator at an RF frequency to generate an RF electric-magnetic field sufficient to generate an electrical discharge in the high pressure gas. The electrical discharge produces an emission spectrum that may be spectroscopically analyzed to determine the composition and impurity content of the gas.

22 Claims, 6 Drawing Sheets

U.S. PATENT DOCUMENTS

| | | |
|---|---|---|
| 5,841,243 A | 11/1998 | Hooper |
| 5,953,360 A * | 9/1999 | Vitruk et al. .................. 372/87 |
| 6,017,221 A | 1/2000 | Flamm |
| 6,100,650 A | 8/2000 | Yokozeki et al. |
| 6,127,275 A | 10/2000 | Flamm |
| 6,137,237 A * | 10/2000 | MacLennan et al. ........ 315/248 |
| 6,236,457 B1 * | 5/2001 | Allen et al. ................. 356/328 |
| 6,309,385 B1 | 10/2001 | Simpson |
| 6,483,259 B1 | 11/2002 | Kramer |
| 6,504,307 B1 * | 1/2003 | Malik et al. ............ 315/111.21 |
| 2001/0033813 A1 | 10/2001 | Filho et al. |
| 2002/0153101 A1 | 10/2002 | Nguyen et al. |

OTHER PUBLICATIONS

Copies of PCT ISR and WOISA for PCT/US05/09063, No Date.

* cited by examiner

SYSTEM AND METHOD FOR GENERATING A DISCHARGE IN GASES

RELATED APPLICATIONS

This application claims the benefit of U.S. Provisional Patent Application Ser. No. 60/553,971 filed Mar. 18, 2004 and Ser. No. 60/648,417 filed Feb. 1, 2005, the content of each is incorporated herein by reference. This application is a continuation-in-part of U.S. patent application Ser. No. 10/939,338 filed Sept. 14, 2004, which is a continuation of U.S. patent application Ser. No. 10/112,349 filed Apr. 1, 2002, now U.S. Pat. No. 6,791,280. The content of all related applications is incorporated herein by reference.

FIELD OF THE INVENTION

The present invention relates to gas composition analysis. More particularly the present invention relates to nondestructive analysis of high pressure gas contained in dielectric enclosures by emission spectroscopy.

BACKGROUND OF THE INVENTION

Metal halide and other high intensity discharge (HID) lamps have found widespread acceptance for lighting large area indoor and outdoor spaces. In the manufacture of HID lamps, it is often desirable to provide a controlled atmosphere for many of the components of the lamp to prevent premature failure of the components and thereby prolong the operating life of the lamp. For example, the exposure of the arc tube of an HID lamp to small amounts of oxygen during lamp operation will significantly degrade the components leading to lamp failure, thus shortening the operating life of the lamp. Further by way of example, the exposure of the arc tube to hydrogen may lead to diffusion of hydrogen into the arc tube leading to high starting and re-ignition voltages, and ultimately reduced life expectancy of the lamp. To prevent the exposure of such components to damaging atmospheres, it is well known to provide a controlled atmosphere for the components by enveloping the components in a desired atmosphere contained within an outer lamp jacket. Typically, the outer jacket of an HID lamp is filled with an inert gas such as nitrogen.

In view of the deleterious effects of the presence of impurities, it is desirable to nondestructively analyze the composition and impurity content of the gaseous atmosphere contained within the lamp outer jackets. Gas analysis by emission spectroscopy is well known in analyzing the composition and impurity content of gaseous atmospheres at low pressures (<about 0.1 atm). However, the gaseous atmosphere contained within an outer jacket of an HID lamp is typically at relatively high pressure (about 0.1–2.0 atm). There remains a need for nondestructive gas analysis by emission spectroscopy in high pressure gaseous atmospheres.

Accordingly, it is an object of the present invention to obviate the deficiencies of the prior art and to provide a novel system and method for nondestructive high pressure gas analysis.

It is another object of the present invention to provide a novel system and method for generating a discharge in a high pressure gas.

It is a further object of the present invention to provide a novel system and method for creating a stable electrical discharge in a high pressure gas contained in a sealed enclosure, so that the composition and impurity content of the gas can be spectroscopically analyzed without destroying the enclosure.

It is yet another object of the present invention to provide a novel system and method for emission spectroscopy of gaseous atmospheres.

It is yet another object of the present invention to provide a novel system and method for nondestructive analysis of HID lamps.

These and many other objects and advantages of the present invention will be readily apparent to one skilled in the art to which the invention pertains from a perusal of the claims, the appended drawings, and the following detailed description of the preferred embodiments.

DETAILED DESCRIPTION OF THE INVENTION

The present invention generally finds utility in generating a discharge in high pressure gas. By way of example only, certain aspects of the invention will be described in connection with emission spectroscopy for nondestructive analysis of the gaseous content in HID lamps.

According to one aspect, the present invention provides a high Q, single frequency RF discharge source for generating a small localized and stable electrical discharge (plasma) in a high-pressure (0.1 atm to 2 atm) gas contained within the outer jacket of an HID lamp. The discharge source includes a helical coil resonator (HCR) for providing sufficient RF energy to generate the discharge. The optical emission spectrum from the plasma can then be spectroscopically analyzed to determine the composition of the gas and the gaseous impurity content within the enclosure. Impurity concentrations less than about 0.01 percent by volume may be detected. Typically the gaseous atmosphere comprises $N_2$, and may include gaseous impurities such as $O_2$, $H_2$, $CO_2$, CO, $H_2O$, $CH_4$, and the like, which contain elements such as O, H, C, and/or any combinations thereof. The RF discharge source of the present invention is capable of establishing and maintaining a discharge in high pressure gas, and consumes very little power, thus being useful in both lab and production line applications.

The RF discharge source creates an electrical discharge inside the enclosure by generating an RF electric-magnetic (electric) field that penetrates through the dielectric wall of the enclosure. The electric field required for the discharge is proportional to E/N, where E is the electric field strength and N the number density of the gas. The gas pressure inside the outer jacket of a HID lamp is typically about 0.5 atm at room temperature, requiring a field strength of about 7 kV/cm to establish a discharge. When a discharge is established, the heat generated by the discharge reduces the gas number density (N) thus requiring less electric field strength (E) to maintain the discharge.

The optical emission spectrum of the plasma, i.e., the atomic and molecular emission of species in the excited plasma, is analyzed using conventional spectroscopic techniques to determine the composition and impurity content of the high pressure gas in the enclosure. This typically involves recording the optical emission spectrum of the plasma at UV, visible, and near-IR wavelengths at sufficiently high resolution to resolve the atomic lines of the impurities of interest. The spectrum is analyzed by visual/graphical and/or computer aided data manipulation to measure the magnitude of the spectral peaks of interest. This data is compared to similar data collected from known standards of the impurities of interest. The concentrations of the impurities are then calculated by comparison to the known standards.

Figure 1:
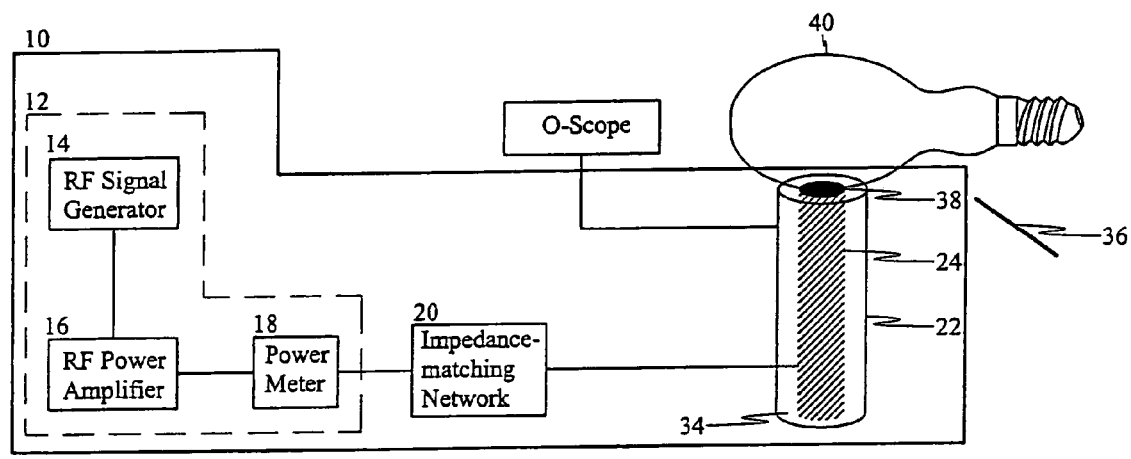
FIG. 1 is a schematic diagram illustrating an RF discharge source according to an exemplary embodiment of the present invention.

FIG. 1 schematically illustrates the RF discharge source 10 according to an exemplary embodiment of the present invention. The RF discharge source 10 is capable of producing the several thousand volts needed to strike a discharge in a high pressure gas contained in a sealed enclosure. The RF discharge source 10 comprises an RF power generator 12, an impedance-matching network 20, and an HCR 22. The RF power generator 12 includes an RF signal generator 14, an RF power amplifier 16, and power meter 18. The RF power generator 12 typically outputs about a few hundred volts and drives the HCR 22 at RF frequencies from about 100 kHz to greater than 100 MHz, and typically about 10 MHz. The HCR 22 operates like a combination of an open-circuited quarter-wave transmission line in parallel with an inductor back to ground to step up the voltage from the RF power amplifier 16 by factors of 20 to 100 or greater.

Figure 2:
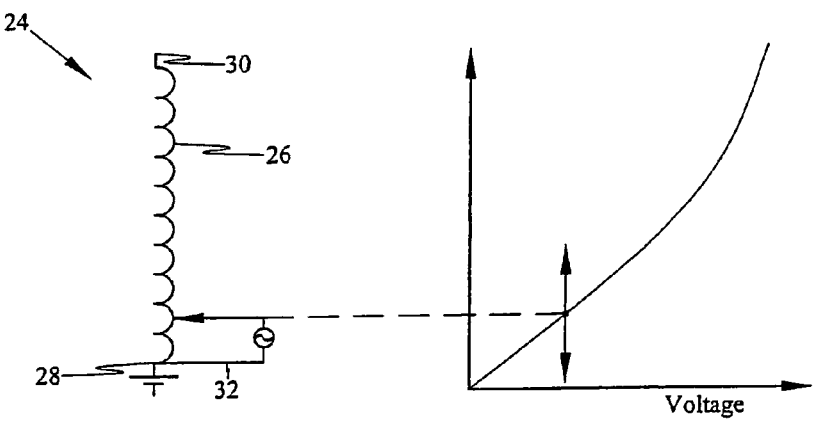
FIGS. 2 and 3 are schematic diagrams illustrating an exemplary helical coil resonator.

The HCR 22 typically includes a wire helix 24 and an electrically conductive shield 34. As illustrated in FIG. 2, the wire helix 24 is formed by a conductive spiral coil 26 having a first end 28 connected to ground and a second opposing end 30 serving as an electrode. An input tap 32 is located on the coil 26 between the ground (the first end of the coil 28) and a point close to the ground.

Referring again to FIG. 1, the enclosure or outer jacket 40 to be analyzed is placed in contact with the electrode 30 where the RF voltage is highest. The RF electric field penetrates through the dielectric wall of the enclosure 40 to generate a very stable discharge inside the enclosure 40. A discharge within the outer jacket of an HID lamp may be generated without exciting the gaseous contents of the arc tube (not shown), which typically contains a low pressure gas such as Ar and a low pressure vapor such as Hg. The high voltage at the electrode 30 is a result of the RF power injected at a tap close to the ground point. In one embodiment, a fiber optic light gathering device 36 collects the optical emission spectrum of the plasma in the UV, visible, and near IR wavelength ranges, for analysis.

As discussed above, the operation of the HCR 22 is similar to a transformer, with the voltage being stepped up by the turns ratio of the coil 26. However, the operation of the HCR 22 is frequency dependent, and its operation may best be modeled by a transmission line cavity having a wire length L in the coil (illustrated in FIG. 2 measured from the tap point or first end 28 of the coil 26 to the electrode or second end 30 of the coil 26) being slightly less than one quarter of an RF wavelength. In one embodiment of the present invention, a coil length L of about 5.5 meters is suitable for an operating frequency of about 13.6 MHz (which is set to operate within the allowable FCC bandwidth). It should be understood that the coil length and operating frequency are not limited to these values.

Figure 3:
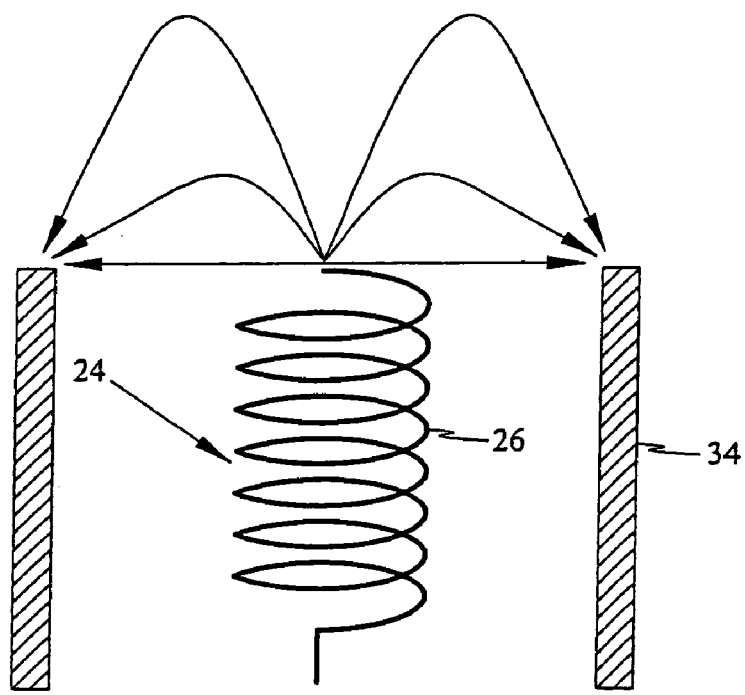

The electrically conductive shield 34 is typically formed from metal to enclose the coil 26 as illustrated in FIG. 3 and provides the return path for the RF current. The combination of the RF shield 34, coil, and the selection of the tap point 32 enable the HCR 22 to exhibit a Q of between about 500 and about 900.

Referring again to FIG. 2, the input signal is connected to the input tap 32 between the ground and a point close to the ground. Since the total coil length L is about one quarter of the wavelength of the RF electric field, the highest electric field strength is located at the electrode 30 formed by the other end of the coil 26. The electric field strength may be raised or lowered by raising or lowering the electric field strength at the input tap 32.

The impedance-matching network 20 matches the input impedance of the HCR 22 to the output impedance of the RF power generator 12 at the frequency of operation. In one embodiment, the matching impedance may be about 50 ohms. At RF frequencies, the input impedance contains both resistance and reactance. The matching network 20, made up of inductance and capacitance, may be designed to modify the HCR input impedance to be about 50 ohms. Moreover, the location of the input tapping point 32 should also be considered in matching the input impedance of the HCR 22 to the output impedance of the RF power generator 12.

Figure 4:
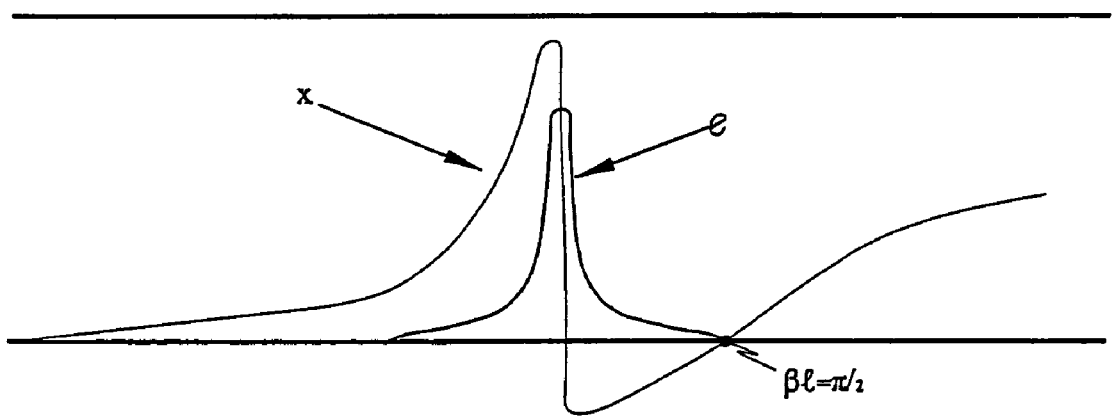
FIG. 4 is a graph illustrating the impedance of a helical coil resonator as a function of frequency at the driving point.

Specifically, the open circuit coil can be viewed as an open-circuit transmission line that is about one quarter wavelength in length. Since the coil 26 is open circuited, the driving point impedance $Z_d$ of the open part of the circuit is approximately:

$$Y_d = +j\ Y_0 \tan \beta l,\ Z_d = -j\ Z_0 \cot \beta l$$

where $Y_0 = 1/Z_0$, $Z_0$ = characteristic impedance of the helical transmission line, l is the length from the driving point to the tip of the electrode, and $\beta$ is the phase constant. The impedance as a function of frequency at the driving point is measured and plotted in FIG. 4. This $Z_d$ contains both the real part and imaginary parts. In order to match the output impedance of the RF source (50 ohms), a properly-designed impedance matching network that consists of capacitors and inductors is inserted between the RF source and the driving point of the HCR to obtain the maximum delivery of power of the RF source to the HCR.

The RF discharge source 10 may be operated by first adjusting the frequency of the RF signal 14 generator to match the resonant frequency of the HCR 22. Alternatively the tap point, coil spacing or other dimensions of the HCR 22 can be adjusted to match the (fixed) frequency of the RF signal generator 14. In one embodiment, the combination of the RF signal generator 14 and RF power amplifier 16 of the RF power generator 12 produces a sinusoidal voltage of about 300 Volts (rms). The power generated at the output of the amplifier 16 passes through the power meter 18, which is capable of measuring both forward and reflected wave powers.

The power subsequently goes through the matching network 20 before it couples to the HCR 22. The matching network 20 includes a variable capacitor (not shown) which allows the matching impedance of the matching network 20 to be selectively adjusted by tuning the capacitor in order for the electrode 30 of the coil 26 to reach its highest voltage. The impedance matching network 20 is adjusted to minimize reflected power and maximize "forward" power into the plasma load and to maximize the physical and temporal stability of the plasma.

An electric field pick-up device 38 may be provided to monitor the electrode voltage. The electric field pick-up device 38 includes a metal plate soldered to the center conductor of a coaxial connector positioned near the electrode 30. In one embodiment, the signal from the capacitance pickup may be used to maximize the voltage at the electrode 30 as the matching network components are changed.

It may be necessary in some instances to reduce the heating effect of the RF discharge on the dielectric surface of the enclosure containing the gas to be analyzed. The RF signal generator 14 may include a gate feature that allows an RF waveform to be duty-cycle modulated. A suitable modulation frequency may be between 10 and 1000 Hz, and typically about 120 Hz, and a duty cycle between 1 percent and 99 percent, and typically about 10 percent. The pulsed RF discharge reduces the heating effect of the discharge on dielectric enclosure. In addition to reducing the duty cycle of the continuous RF waveform, the gated RF allows analysis of optical emission from excited atoms or molecules which persist and radiate in the afterglow during the period when the RF source is gated to the "off" state.

In embodiments of the present invention for generating a discharge in gases at pressures over about 300 torr, a Tesla coil (not shown) has been found to be suitable for initiating the discharge.

Figure 7:
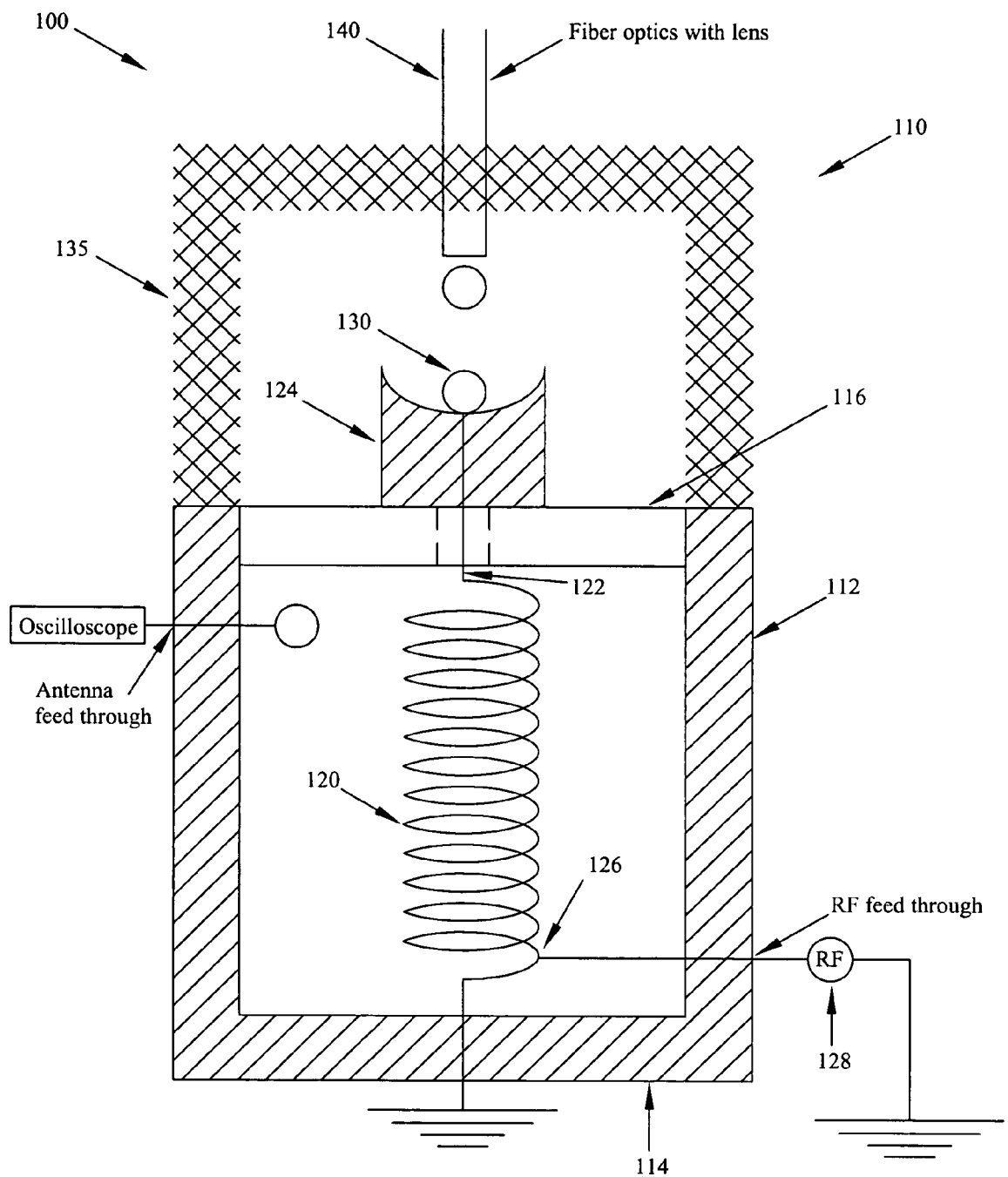
FIG. 7 is an illustration of a system for atomic emission spectroscopic analysis of the gaseous content of a vessels according to one aspect of the present invention.

FIG. 7 illustrates another embodiment of the present invention. With reference to FIG. 7, the system 100 for atomic emission spectroscopic analysis of the gaseous content of a vessel includes the device 110 for generating an electric discharge one or more vessels 130, a Faraday cage 135, fiber optics 140 for collecting the spectral information, and a spectrophotometer (not shown) for measuring the spectral information.

The device 110 includes an electrically conducting housing 112. The housing 112 is typically circular in horizontal cross-section, but may be any suitable shape. The housing 112 is closed at one end by an electrically conducting closure 114 and at the other end by a dielectric cap 116. The dielectric cap 116 may be formed from any suitable material such as teflon. An electrically conducting wire helix 120 is positioned within the housing 112. The wire helix 120 forms an electrode 122 at one end positioned proximate the dielectric cap 116. In the embodiment illustrated in FIG. 7, the electrode 122 extends through the dielectric cap 116 and connects to an electrically conducting element 124 positioned external to the housing 112. The element 124 may be formed from any suitable electrically conducting material.

In one embodiment, the element 124 may be shaped to facilitate contact with a vessel 130 supported thereon for measurement. The shape of the element 124 may also facilitate positioning of the vessel 130 supported thereon relative to the fiber optic 140 to assist in coupling the light emitted from the vessel 130 into the fiber optic 140. For example, the upper surface of the element 124 may be concave forming a bowl so that a vessel supported thereon will rest at the bottom of the bowl.

The wire helix 120 includes an RF power receiving tap 126 near the other end of the wire opposite the electrode 122. The RF power source 128 is connected to the tap 126.

The device 110 is suitable for generating an electric discharge in vessels having a dielectric wall and a gaseous content having a pressure as low as a fraction of a torr, or up to 2 atmospheres or more. The device 110 is particularly suitable for atomic emission spectroscopic analysis of arc tubes for HID lamps.

Figure 8:
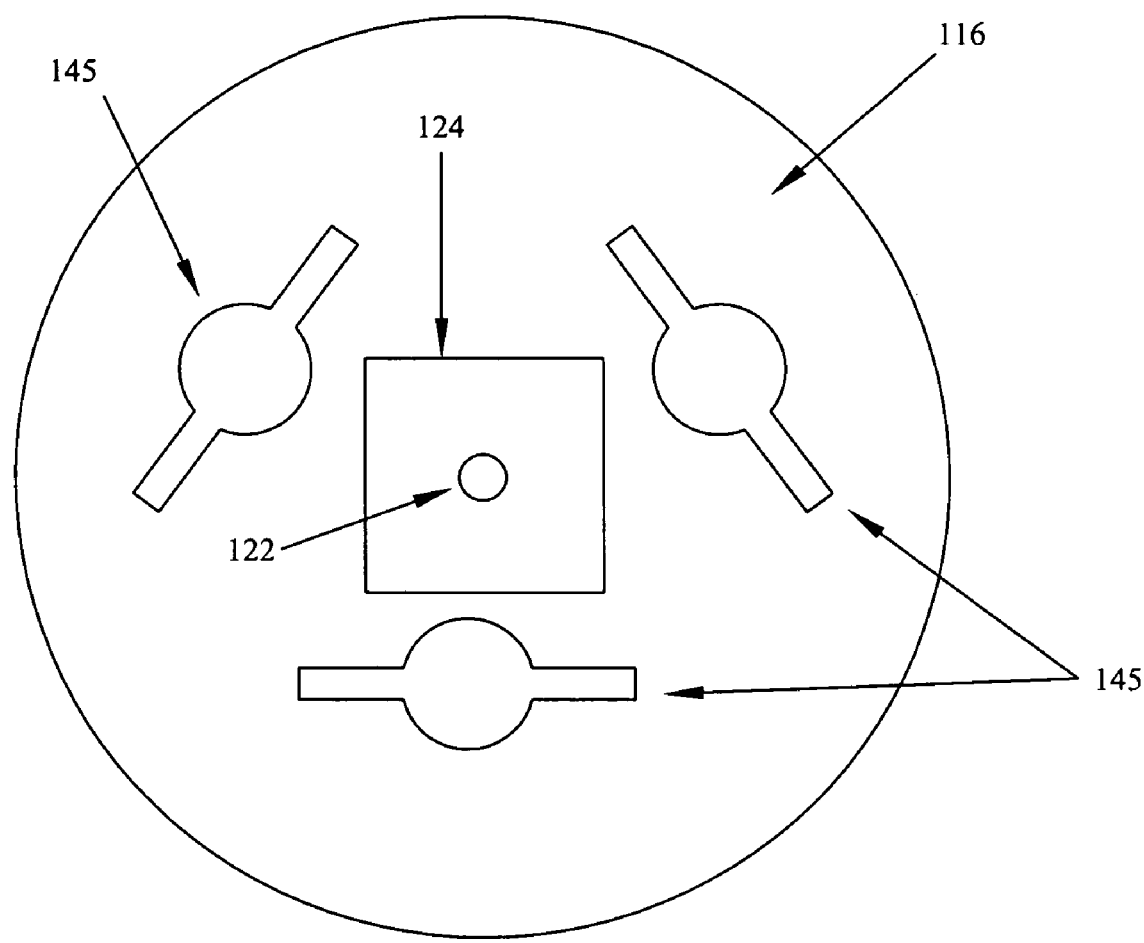
FIG. 8 is a top view of the system illustrated in FIG. 7.

In another aspect of the present invention, the system 100 may be used to analyze the content of a plurality of vessels simultaneously. With reference to FIG. 8, a plurality of vessels 145 (for example HID arc tubes) may be positioned on the dielectric cap 116 in sufficient proximity to the electrode 122 and element 124 to generate a discharge in each vessel. In one example, an electric discharge was generated sufficient for spectroscopic analysis in an arc tube containing argon at a pressure of 50 torr positioned about 2 cm from the element 124 in contact with the electrode 122.

A single fiber optic collector (not shown) may be moved from vessel to vessel to serially collect the spectral information from each vessel. Alternatively, the system may include a fiber optic collector positioned proximate to each vessel being measured so that the spectral information mat be collected simultaneously from each vessel.

EXPERIMENTAL RESULTS

Figure 5:
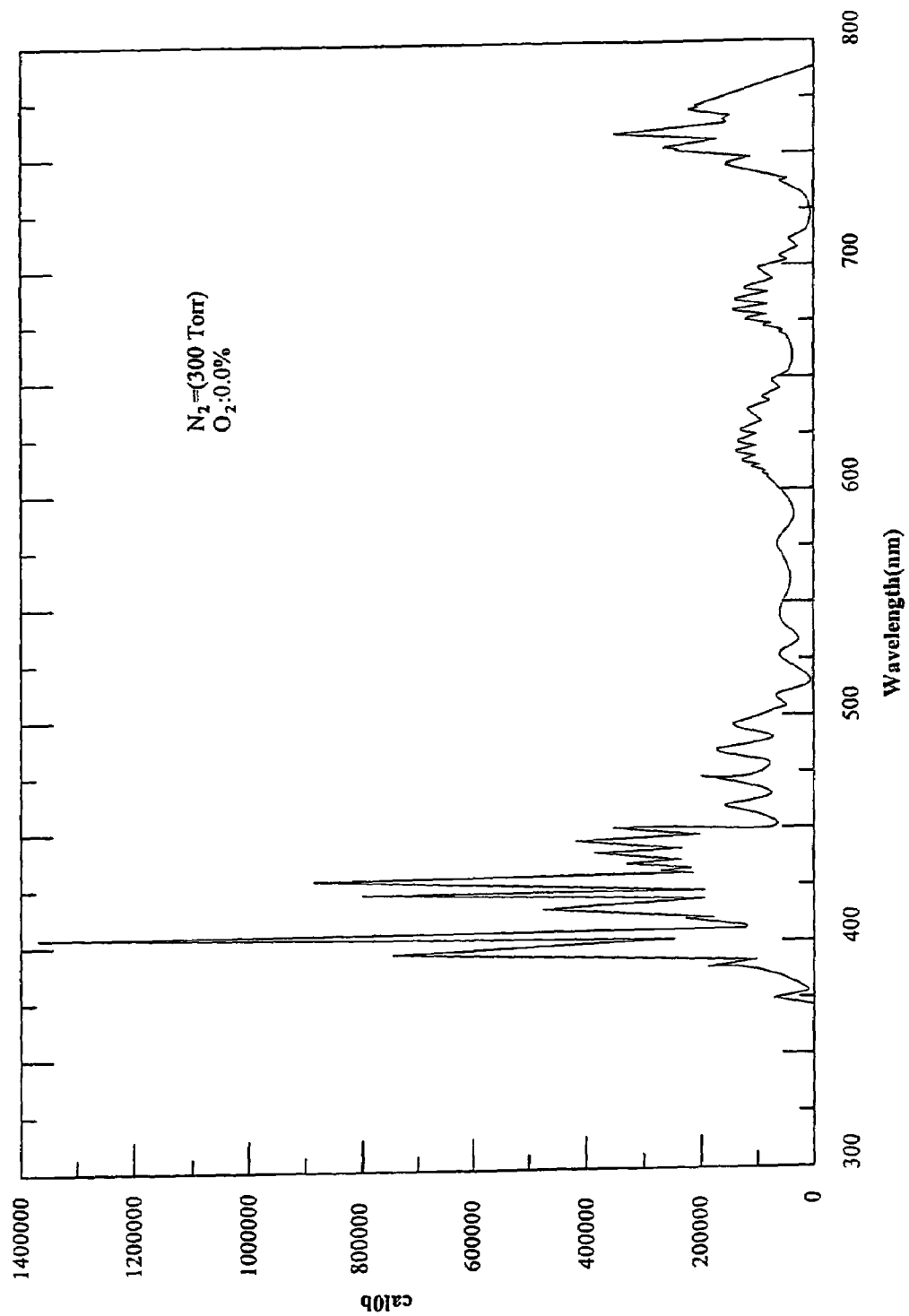
FIG. 5 is a graph illustrating a spectrum from a discharge in pure $N_2$ gas at 0.3 atm (300 torr).
Figure 6A:
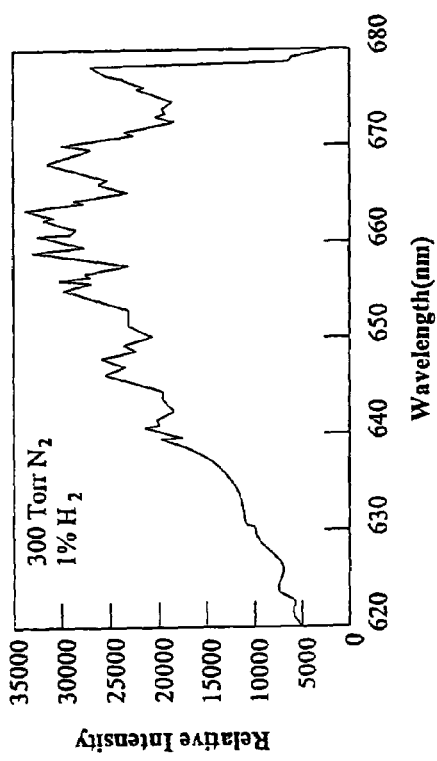
FIG. 6A is a graph illustrating a typical emission spectrum from a helical coil resonator RF discharge in $N_2$ gas and 1 percent hydrogen at 0.3 atm (300 torr).
Figure 6B:
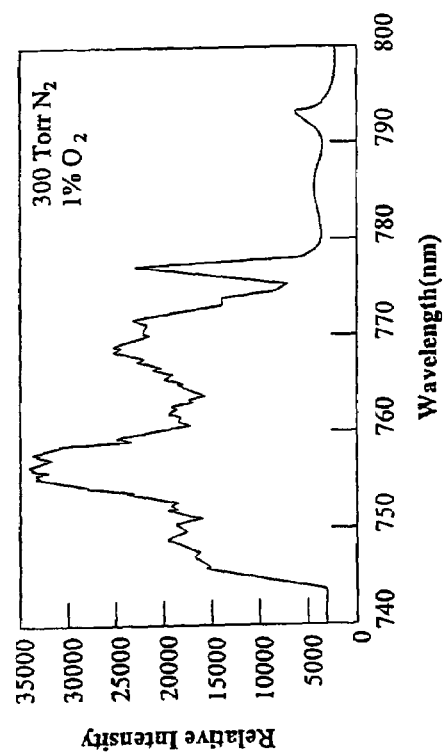
FIG. 6B is a graph illustrating a typical emission spectrum from a helical coil resonator RF discharge in $N_2$ gas and 1 percent oxygen at 0.3 atm (300 torr).

Emission spectra were recorded using an Acton Spectra-Pro 300i spectrophotometer over a range of 350 nm to 900 nm with a resolution of 0.4 nm FIG. 5 illustrates a spectrum from a discharge in pure $N_2$ gas at 300 torr. FIG. 6A illustrates the analytically useful lines of atomic hydrogen (656 nm) and FIG. 6B illustrates the analytically useful lines of atomic oxygen (777 nm) from standards of known 1% hydrogen and 1% oxygen in nitrogen at 300 torr. These atomic lines can be seen as relatively sharp peaks superimposed on the complex nitrogen molecular band spectra. Detection limits for oxygen and hydrogen in a fill comprising nitrogen at 500 torr include about 0.3% and 0.1% by volume respectively.

While preferred embodiments of the present invention have been described, it is to be understood that the embodiments described are illustrative only and the scope of the invention is to be defined solely by the appended claims when accorded a full range of equivalence, many variations and modifications naturally occurring to those of skill in the art from a perusal hereof.

What is claimed is:

1. A device for generating an electrical discharge in a gas sealed within an enclosure having a dielectric wall, said device comprising:
    an elongated electrically conducting housing;
    a dielectric cap enclosing one end of said housing;
    an electrically conducting wire forming a helix axially positioned within said housing, said wire forming an electrode at one end positioned proximate said dielectric cap and having an RF power receiving tap near an other end; and
    an RF power source connected to said tap and providing RF power to generate an RF field in proximity to the electrode having sufficient strength to effect a discharge in the gas sealed within the enclosure.

2. The device of claim 1 wherein a length of the wire between the electrode and the tap is about one quarter a wavelength of the RF power.

3. The device of claim 1 wherein a voltage of the RF power at the electrode is at least twenty times greater than the voltage of the RF power at the tap.

4. The device of claim 3 wherein the voltage of the RF power at the electrode is at least one hundred times greater than the voltage of the RF power at the tap.

5. The device of claim 1 wherein said dielectric cap comprises teflon.

6. The device of claim 1 wherein said housing comprises an electrically conducting generally cylindrical wall.

7. The device of claim 1 wherein said electrode extends through said dielectric cap and connects to an electrically conducting element positioned external to said housing.

8. The device of claim 7 wherein said electrically conducting element includes a concave surface.

9. A system for generating a discharge in the gaseous content of a vessel, said system comprising:
   a vessel having a dielectric wall;
   one or more gasses contained in said vessel;
   an RF generator for generating an RF field sufficient to effect a discharge in said gas, said generator comprising:
      an RF power source; and
      a helical coil resonator, said resonator being connected at one end to said RF power source and forming an electrode at an other end thereof, said electrode being external to said vessel and in sufficient proximity to said dielectric wall of said vessel to establish a discharge in said gas.

10. The system of claim 9 comprising a plurality of vessels each having a dielectric wall and a gaseous content, each of said vessels being positioned in sufficient proximity to said electrode to establish a discharge in the gas contained in said vessel.

11. The system of claim 9 wherein a pressure of the gas contained in said vessel in at least 20 torr.

12. The system of claim 11 wherein the pressure of the gas contained in said vessel in at least 50 torr.

13. The system of claim 9 wherein a portion of the dielectric wall of said vessel is positioned within about 2 cm from said electrode.

14. A system for atomic emission spectroscopic analysis of the gaseous content of a vessel, said system comprising:
   one or more vessels having a dielectric wall and containing a gaseous content;
   a device for generating an electric discharge in the gaseous content of said vessel, said device comprising:
   an elongated electrically conducting housing;
   a dielectric cap enclosing one end of said housing;
   an electrically conducting wire forming a helix axially positioned within said housing, said wire forming an electrode at one end positioned proximate and an other end of said housing enclosed by said dielectric cap and having an RF power receiving tap near the other end;
   an RF power source connected to said tap; and
   a spectrophotometer,
   wherein said vessel is positioned in sufficient proximity to said electrode so that the RF field generated at the electrode effects a discharge in the gaseous content of said vessel.

15. The system of claim 14 comprising a plurality of vessels each positioned in sufficient proximity to said electrode so that the RF field generated at the electrode effects a discharge in the gaseous content of said vessels.

16. The system of claim 14 wherein said electrode extends through said dielectric cap and connects to an electrically conducting element.

17. The system of claim 16 wherein said electrically conducting element includes a vessel supporting portion having a curved surface.

18. The system of claim 16 wherein said electrically conducting element includes a vessel supporting portion having a v-shaped groove.

19. The system of claim 16 comprising a plurality of vessels each positioned in sufficient proximity to said electrically conducting element so that the RF field generated at the element effects a discharge in the gaseous content of said vessels.

20. A system for atomic emission spectroscopic analysis of the gaseous content of a vessel, said system comprising:
   one or more vessels having a dielectric wall and containing a gaseous content;
   a device for generating an electric discharge in the gaseous content of said vessel, said device comprising:
   a generally cylindrical electrically conducting housing;
   a dielectric cap enclosing one end of said housing;
   an electrically conducting wire forming a helix axially positioned within said housing, said wire forming an electrode at one end extending through said dielectric cap and having an RF power receiving tap near the other end;
   an electrically conducting element connected to said electrode, said element being positioned on an external surface of said dielectric cap and having a vessel supporting portion having a curved surface;
   an RF power source connected to said tap;
   a spectrophotometer; and
   a fiber optic for transporting light emitted from said vessel to said spectrophotometer,
   wherein said one or more vessels are positioned in sufficient proximity to said electrically conducting element so that the RF field generated at the electrode effects a discharge in the gaseous content of said vessels.

21. The system of claim 20 wherein said vessel is supported by said curved surface of said electrically conducting element.

22. The system of claim 20 where a plurality of vessels are supported on the external surface of said dielectric cap.

* * * * *